Figure 1:
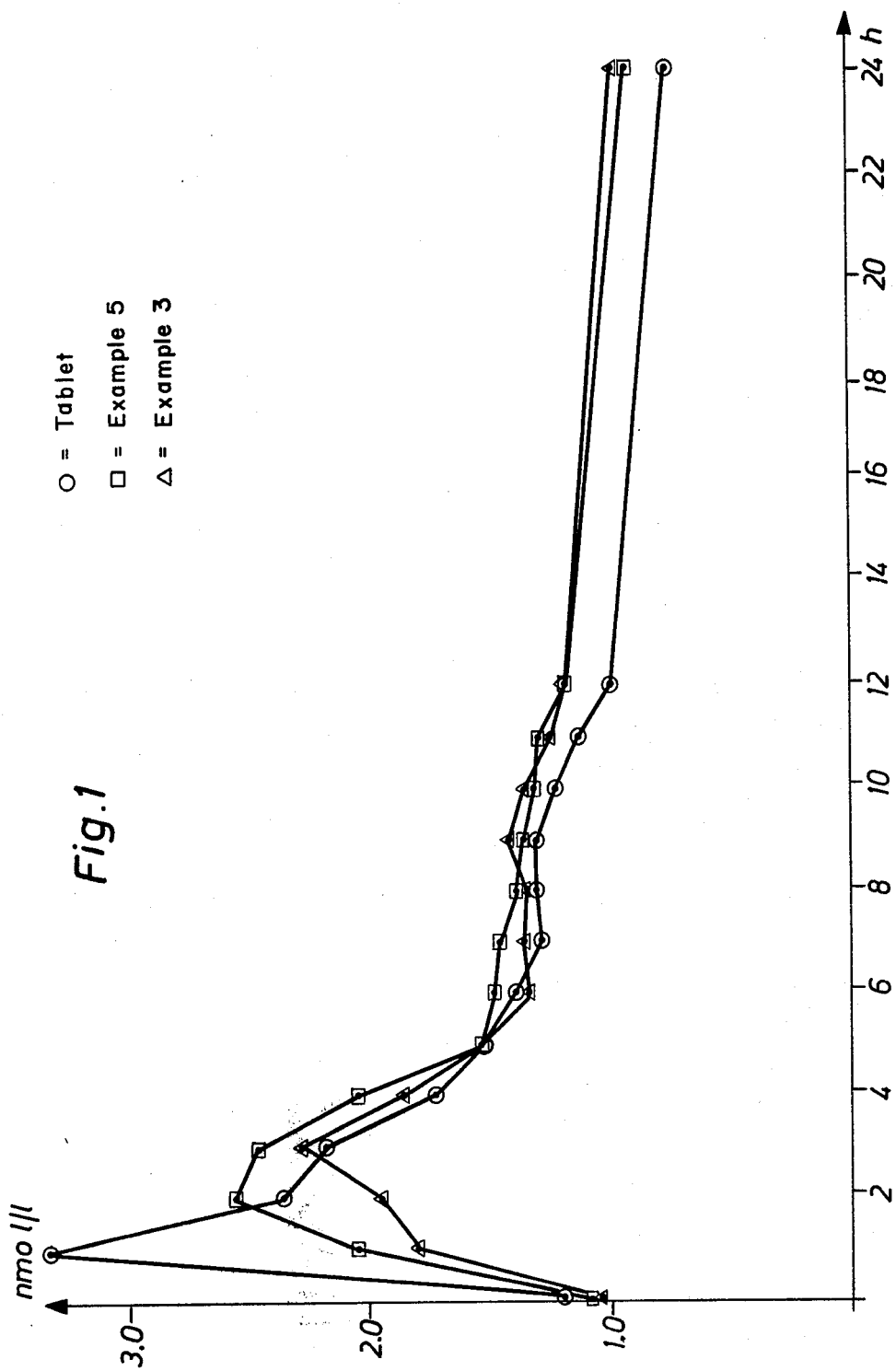

United States Patent [19]

Appelgren et al.

[11] 4,263,273
[45] Apr. 21, 1981

[54] PHARMACEUTICAL PREPARATION COMPRISING A CARDIAC GLYCOSIDE WITH A POLYMER COATING

[75] Inventors: Curt H. Appelgren, V Frölunda; Conny B. Bogentoft, Kållered; John A. Sjögren, Mölnlycke, all of Sweden

[73] Assignee: Aktiebolaget Astra, Molndal, Sweden

[21] Appl. No.: 104,689

[22] Filed: Dec. 17, 1979

[30] Foreign Application Priority Data

Dec. 22, 1978 [SE] Sweden ............................. 7813246

[51] Int. Cl.³ .................... A61K 9/22; A61K 9/24; A61K 31/705
[52] U.S. Cl. ........................................ 424/21; 424/19; 424/20; 424/32; 424/33; 424/35; 424/182
[58] Field of Search .................... 424/19–22, 424/32, 33, 182, 35

[56] References Cited

U.S. PATENT DOCUMENTS

| | | | |
|---|---|---|---|
| 2,455,790 | 2/1948 | Malm et al. | 424/33 |
| 2,698,822 | 1/1955 | Halpern et al. | 424/182 |
| 2,702,264 | 2/1955 | Klaui | 424/33 |
| 2,853,420 | 9/1958 | Lowey | 424/35 |
| 2,881,085 | 4/1959 | Endicott et al. | 424/35 |
| 2,921,883 | 1/1960 | Reese et al. | 424/21 |
| 2,928,770 | 3/1960 | Bardani | 424/21 |
| 3,080,294 | 3/1963 | Shepard | 424/21 |
| 3,089,824 | 5/1963 | Wurster | 424/35 |
| 3,247,066 | 4/1966 | Milosovich | 424/35 |
| 3,325,365 | 6/1967 | Hotko et al. | 424/33 |
| 3,344,029 | 9/1967 | Berger | 424/35 |
| 3,371,015 | 2/1968 | Sjogren et al. | 424/33 |
| 3,400,185 | 9/1968 | Kohnle et al. | 424/35 |
| 3,538,214 | 11/1970 | Polli et al. | 424/35 |
| 3,775,537 | 11/1973 | Lehmann et al. | 424/21 |
| 3,835,221 | 9/1974 | Fulberth et al. | 424/35 |
| 3,954,959 | 5/1976 | Pedersen | 424/21 |
| 3,965,255 | 6/1976 | Bloch et al. | 424/33 |
| 4,083,949 | 4/1978 | Benedikt | 424/35 |
| 4,147,768 | 4/1979 | Shaffer et al. | 424/35 |
| 4,151,273 | 4/1979 | Riegelman et al. | 424/78 |

FOREIGN PATENT DOCUMENTS 2651176  5/1977  Fed. Rep. of Germany .

OTHER PUBLICATIONS

Bogentoft et al., Chem. Abstracts 87 #73374f (1977) abstract of Ger. Off. 2,651,176, 18 May 1977, 18 pp. based on Swed. Appl. 75/12,883, 17 Nov. 1975.
Bogentoft et al., Chem. Abstracts 90, #76495u (1979), abstract of Evr. J. Clin. Pharmacol. 14(5):351-5 (1978) (Enteric Coated Granules Permit More Reproducible Absorption than Enteric Coated Tablets, When Taken with Food).

Primary Examiner—Shep K. Rose
Attorney, Agent, or Firm—Brumbaugh, Graves, Donohue & Raymond

[57] ABSTRACT

A solid pharmaceutical preparation for administration in dosage unit form comprising a therapeutically effective cardiac glycoside, whereby each dosage unit is to comprise a plurality of bodies, each of said bodies having a pharmaceutically indifferent core, a first layer thereon containing the glycoside and a second layer containing a polymer insoluble in gastric juice and soluble in intestinal juice, a process for preparing such preparation and a method of treatment employing the same.

9 Claims, 1 Drawing Figure

PHARMACEUTICAL PREPARATION COMPRISING A CARDIAC GLYCOSIDE WITH A POLYMER COATING

DESCRIPTION

1. Technical Field

The present invention is related to a novel pharmaceutical preparation comprising a digitalis glycoside or a similar compound effective in the treatment of cardiac disorders, and a process for producing such preparation, and a method of treatment using such preparation.

An object of the invention is to provide a pharmaceutical preparation in which a cardiac glycoside comprised therein is protected against substantial decomposition in the acid environment of the stomach of a mammal including man, without loss of bioavailability on release and intestinal absorbtion.

A further object is to provide a pharmaceutical preparation giving a sustained or controlled release of a cardiac glycoside comprised therein without loss of bioavailability.

2. Background Art

Digitalis glycosides or cardiac glycosides constitute a class of drugs among which are a few of the oldest drugs in current use. Their main utility is in the treatment of cardiac disorders such as cardiac insufficiency and cardiac arrythmias. The term "cardiac glycosides" as used herein includes therapeutically effective naturally occurring digitalis glycosides and similar compounds of different origin including compounds preparable as semisynthetic derivatives of naturally occurring compounds, irrespective of the manner of obtention thereof. Below, the cardiac glycosides are occasionally referred to as "the active ingredient".

Cardiac glycosides are broken down in an acid environment. This effect is seen especially with digoxin, lanatoside C, digitoxin and proscillaridin.

Thus digoxin is hydrolysed very rapidly in a buffer solution of pH 1 leaving only 10% thereof after exposure for 1 hour. Such decomposition also takes place in vivo; thus it is described that 40% of a given dose may be broken down. As some of the products of hydrolysis have a substantially lower biological activity than has the mother substance this means that the therapeutical response of a given dose of cardiac glycosides may vary between individuals and between moments of administration depending on how long the preparation stays in the stomach and what pH is prevailing at the time of passage.

It is, however, known in the literature that conventional gastric juice resistant preparations of digitalis glycosides such as tablets provided with a conventional enteric coating give an impaired bioavailability of the glycoside. The fact that digitalis glycosides are difficultly soluble in aqueous media make them further difficult to include in pharmaceutical preparations while obtaining a satisfactory bioavailability.

Digitalis glycosides in general have a narrow therapeutical index, i.e. the dose thereof producing toxic or other undesirable side effects is not much greater than the therapeutically effective dose. Several side effects e.g. nausea and arrythmias encountered in treatment with cardiac glycosides are related to a peak in plasma concentration often occurring a few hours after administration of a dose. For these reasons it is strongly desirable to prepare compositions giving a sustained release of the cardiac glycosides. Bio-pharmaceutical studies have, however, shown that hitherto known sustained release preparations have the drawback of giving an impaired bioavailability of the digitalis glycoside.

DISCLOSURE OF INVENTION

The present invention is related to a pharmaceutical preparation for oral administration in dosage unit form. The pharmaceutical preparation of the invention comprises a cardiac glycoside with a polymer coating, and is characterized in that said pharmaceutical preparation is in the form of a plurality of small bodies, each body comprising a fraction of a therapeutically effective dosage of the cardiac glycoside, whereby each body has a core made up of pharmaceutically indifferent material, and on said core a first layer made up of a composition comprising the cardiac glycoside, and thereon a second layer comprising an anionic carboxylic polymer being difficultly soluble or insoluble below a given pH value in the interval of pH 4–7.5 but being soluble at a pH above said given value. Each layer is preferably applied by spraying a solution of the components of the layer.

Normally each dosage unit contains at about 10 to $10^6$ bodies. Preferably the number of bodies is about 200 to 1000. Thus, each body of the preparation shall contain a fraction of a therapeutically effective dosage of the cardiac glycoside. The fraction is normally $1 \cdot 10^{-6}$ to $1 \cdot 10^{-1}$ times such dosage and preferably $1 \cdot 10^{-3}$ to $5 \cdot 10^{-3}$ times such dosage. Among suitable dosage units tablets and capsules are specifically mentioned. Pharmaceutically acceptable additives may be included in the dosage units together with the preparation of the invention. Preparations wherein the solid bodies are in admixture with a liquid medium are also within the scope of the invention.

The cores of the bodies of the preparation may be made up of pharmaceutically indifferent materials in granular or pulverulent form of the type normally used in pharmaceutical preparations, such as sugar, microcrystalline cellulose, starch and waxes. "Pharmaceutically indifferent" means that the materials are indifferent with regard both to the organism treated and the active substance employed. The size of the cores may be sieve fractions between 0.1 and 3.0 mm, preferably between 0.5 and 1.5 mm.

Among active ingredients which may be employed according to the present invention are therapeutically effective compounds containing the ring systems of digitoxigenin

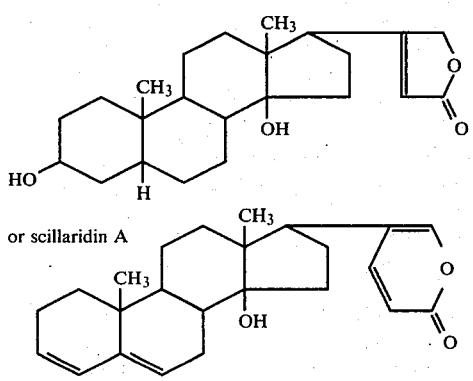

or scillaridin A or derivatives thereof. Of such active ingredients digoxin, digitoxin, lanatoside C, acetyldigoxin, methyldigoxin, proscillaridin, methylprocillaridin, pentaacetylgitoxin, 16-epigitoxin and actodigin are to be specifically mentioned.

According to a preferred embodiment of the invention the first layer mentioned further comprises a water soluble polymer having the ability to increase the solubility or releaseability of the cardiac glycoside in the intestinal juices. Such polymers may be selected from the group of pharmaceutically useful water soluble polymers solid at room temperature comprising polyethylene glycol, polyvinyl-pyrrolidone, the anionic polymers defined below as components of the second layer, and cellulose derivatives such as hydroxypropyl cellulose, methyl cellulose and polyvinyl alcohol.

The polymer substance in the second layer may be selected from the group of anionic carboxylic polymers useful for pharmaceutical purposes and being difficultly soluble at a low pH but being soluble at a higher pH, the pH limit for solubility being in the interval of pH 4 to 7.5, said group comprising celluloseacetate phtalate (CAP)(5.0–5.5), hydroxypropylmethylcellulose phtalate e.g. a quality sold under the name HP-55 (5.0–5.5), polyvinylacetate phtalate (PVAP) (4.5–5.0) and acrylic acid polymers e.g. partly methyl esterified methacylic acid polymers such as Eudragit L (6.0) and Eudragit S (7.0), and methylacrylate-methacrylic acid copolymers such as MPM-05 (5.0). Numbers in brackets above are approximate pH limits. These polymers may be used alone or in combination with each other. The polymers may be admixed with plasticizers such as diethyl or dibutyl phtalates, citric acid esters, e.g. acetyltributyl citrate (Citroflex A-4), stearic acid and fatty alcohols such as cetanol. Suitably the polymer in the second layer is a polymer which is insoluble or difficultly soluble in gastric juice but soluble in intestinal juice. Preferred polymers are CAP, hydroxypropylmethyl-cellulose phtalate, MPM-05 and Eudragit L alone or in combination with each other. Further preferred are Eudragit S in combination with either PVAP or with one of the lastmentioned polymers.

The relative amounts of core material and material constituting the first layer and the second layer may be varied depending i.a. on the properties of the components employed. Preferably the weight of the core relative to the weight of the first layer is 1 to between $2 \cdot 10^{-4}$ and $5 \cdot 10^{-1}$ most preferably 1 to between $2 \cdot 10^{-4}$ and $5 \cdot 10^{-2}$. Preferably the weight of the core plus the first layer relative to the weight of the second layer is 1 to between $1 \cdot 10^{-2}$ and $30 \cdot 10^{-2}$.

The bodies prepared preferably have the size of 0.1 to 3 mm. Their shape, partly dependent on the shape of the cores, is preferably spherical or nearly spherical.

Among the advantages of the preparations of the present invention are to be mentioned that they have an improved biological availability as compared to conventional tablets having an enteric coating. The release of the active component in vitro, at a pH over the pH limit selected e.g. the pH of intestinal juice is rapid with the preparation of the present invention. This is advantageous and accounts in part for the improved bioavailability, however, in vivo a sustained release will occur as the several bodies of the preparation are emptied from the stomach into the small intestine during an extended period of time. The preparation of the invention thereby gives less variation in plasma concentration in patients under continuous treatment that can be obtained with conventional tablets. A further advantage is the improved economy of production that is obtainable while meeting the special demands with preparations of cardiac glycosides.

Another aspect of the present invention is a process for preparing a pharmaceutical preparation for oral administration in dosage unit form. The invention thus provides a process for preparing a pharmaceutical preparation comprising a cardiac glycoside with a polymer coating, said process being characterized in that said pharmaceutical preparation is given the form of a plurality of small bodies, each body comprising a fraction of a therapeutically effective dosage of the cardiac glycoside, by providing a large number of cores made up of pharmaceutically indifferent material, with a first layer made up of a composition comprising the cardiac glycoside, whereupon the bodies comprising said core and first layer are provided with a second layer comprising an anionic carboxylic polymer being difficultly soluble or insoluble below a given pH value in the interval of pH 4–7.5 but being soluble at a pH above said given value. Each of the first layer and the second layer are preferably applied by spraying a solution containing the components of each layer.

According to a preferred embodiment of the invention in said aspect the solution of the digitalis glycoside further comprises a water soluble polymer having the ability to increase the solubility or releasability of the digitalis glycoside in intestinal juices.

All components of the preparation employed by the process of the invention are as further defined above.

The solvents employed according to the process of the invention are solvents having a sufficient volatility to evaporate under the conditions of application, leaving a layer of the solute on the surface of the core or body prepared. Preferably organic solvents such as alcohols, hydrocarbons and esters are used as well as derivatives thereof, such as chlorinated hydrocarbons. The process of applying the layers may be carried out in an apparatus normally used in the pharmaceutical industry for coating of solid pharmaceutical preparations, such as a coating pan or a fluid bed apparatus. The process is normally carried out at ambient conditions, however, temperature and pressure conditions may be varied within broad limits. In a fluid bed spraying process the temperature of the inlet air is suitably 15° to 60° C.

A method of treatment of cardiac disorders employing the pharmaceutical preparation defined above constitutes a further aspect of the invention. The therapeutically effective doses of the cardiac glycosides of the preparations are not greater than those normally prescribed i.e. about 0.05 to 1.5 mg/day for compounds specified herein, subject to variations between different patients. However, it is in many instances possible to employ doses lower than those normally prescribed.

BEST MODE OF CARRYING OUT THE INVENTION

The invention is illustrated by the following examples, of which Example 3 is considered to represent the best mode known at present.

EXAMPLE 1

On spherical granules (700 g. 0.7–1 mm) consisting of microcrystalline cellulose (Avicel ®) 68%, lactose 22% and cetanol 10% a solution of 2.5 g of digoxin and 300 g of polyethylene glycol (Carbowax 6000) in 1000 g of methylene chloride and 1100 g of isopropanol was sprayed. After drying of the granules obtained they were coated by spraying of a solution of 130 g of cellulose-acetate phtalate, 14.4 g of acrylic acid polymer (Eudragit L 90), and 10 g of cetanol in 2056 g of methylene chloride and 1100 g of isopropanol. The process was carried out in a fluidized bed.

In a release test in vitro according to the so called beaker method (Levy et al, New England Journal of Medicine, vol 262, p. 1053–1058 (1960)), referred to as "release test" below, with stirring at 100 rpm in 500 ml of liquid at 37° C. the release of digoxin from the granules was 1% after 10 minutes and 11% after 30 minutes in artificial gastric juice USP pH 1 (referred to as "gastric juice" below) and 53% after 10 minutes and 100% after 30 minutes in a buffer of pH 6.5.

In an absorbtion study the percentage secreted in urine of a digoxin dosage administered with the above preparation and with an aqueous solution was measured. The method of analysis employed does not differentiate between digoxin and its decomposition products. The results were as follows:

| Test person | Aqueous solution | Preparation of Example 1 |
|---|---|---|
| 1 | 45.9 | 58.6 |
| 2 | 51.7 | 42.0 |
| 3 | 46.6 | 41.9 |
| 4 | 54.1 | 44.0 |
| 5 | 33.4 | 41.0 |
| Mean value | 46.2 | 45.5 |

EXAMPLE 2

On sugar granules of the non-pareil type (500 g) a layer of 25 g of polyvinylpyrrolidone and 2.5 g of digoxin is applied and coated with a layer of 72 g of hydroxypropylmethylcellulose phtalate (HP 55) and 5 g of cetanol dissolved in methylene chloride and isopropanol according to the procedure of Example 1.

Release in vitro in percent according to the method referred to in Example 1:

|  | Gastric juice | Buffer pH 6.5 |
|---|---|---|
| 10 minutes | — | 105 |
| 1 hour | 2 |  |
| 2 hours | 7 |  |
| 4 hours | 9 |  |

EXAMPLE 3

Example 2 was repeated modified by using a solution of 25 g of polyethyleneglycol (Carbowax 6000) and 2.5 g of digoxin for the first layer and 36 g polyvinylacetate phtalate and 2.5 g cetanol for the second layer. The release test showed the following release percentages:

|  | Gastric juice | Buffer pH 6.5 |
|---|---|---|
| 10 minutes | — | 71 |
| 0.5 hour | — | 104 |
| 1 hour | 1 | — |
| 2 hours | 3 | — |
| 4 hours | 4 | — |

Amounts of the coated granules thus prepared corresponding to a dose of 0.38 mg digoxin were filled in hard gelatin capsules, size No. 4.

EXAMPLE 4

According to the process of Example 1 a first layer was applied to 500 g of non-pareil sugar granules 0.7–0.84 mm using a solution of 2.5 g of proscilladrin A and 25 g of polyethyleneglycol (Carbowax 6000) in 200 g of methylenechloride and 200 g of isopropanol for building up the first layer and a solution of 36 g of hydroxypropyl-methylcellulose phtalate (HP 55) and 2.5 g of cetanol in 500 g of methylenechloride and 300 g of isopropanol for building up the second layer.

Result of the release test: 26% released after 2 hours in gastric juice and 97% released after 10 minutes in buffer pH 6.5.

EXAMPLE 5

On 500 g of non-pareil sugar granules a first layer was built up by a solution of 2.5 g of digoxin and 25 g of polyethyleneglycol (PEG 6000) in 200 g of methylene chloride and 200 g of isopropanol, whereafter a second layer was built up by a solution of 36 g of HP 55 and 2.5 g of cetanol in 500 g of methylene chloride and 300 g of isopropanol.

The release test showed the following release percentages:

|  | Gastric juice | Buffer pH 6.5 |
|---|---|---|
| 10 minutes | — | 90 |
| 0.5 hour | — | 105 |
| 1 hour | 1 |  |
| 2 hours | 1 |  |
| 4 hours | 2 |  |

Amounts of the coated granules thus prepared corresponding to a dose of 0.38 mg digoxin were filled in hard gelatin capsules, size No. 4.

EXAMPLE 6

On 500 g of non-pareil sugar granules a first layer was applied by a solution of 2.5 g of digoxin in 200 g of methylene chloride and 200 g of isopropanol. A second layer was built up by a solution of 72 g of HP 55 and 5 g of cetanol in 1000 g of methylene chloride and 600 g of isopropanol. The results of the release test were that in gastric juice 2% was released after 4 hours and in buffer pH 6.5 100% was released after 10 minutes.

EXAMPLE 7

On non-pareil cores ($\phi$0.6–0.7 mm) consisting of 30% starch and 70% sugar two layers were coated. The first layer was applied as a solution of digoxin 2.5 g, hydroxypropylmethylcellulose phtalate 12 g and cetanol 0.83 g in methylene chloride 166 g and isopropanol 100 g. The second layer was applied as a solution of hydroxypropyl-methylcellulose phtalate 24 g, and cetanol 1.67 g in methylene chloride 334 g and isopropanol 200 g. Release of digoxin in vitro: artificial gastric juice pH 1,0 <1% after 4 hours, in phosphate buffer pH 6.5 104% after 10 minutes.

EXAMPLE 8

On 500 g of non-pareil sugar granules a first layer was built up by a solution of 2.5 g of digitoxin and 25 g of polyethyleneglycol (PEG 6000) in 200 g of methylene chloride and 200 g of isopropanol, whereafter a second layer was built up by a solution of 36 g of hydroxypropyl-methylcellulosephtalate and 2.5 g of cetanol in 500 g of methylene chloride and 300 g of isopropanol. The results of the release test were that in gastric juice <1% was released after 4 hours and in buffer pH 6.5 78% was released after 30 minutes.

EXAMPLE 9

On 500 g of non-pareil sugar granules a first layer was applied by a solution of 2.5 g of digoxin in 200 g of methylene chloride and 200 g of isopropanol. A second layer was built up by a solution of 72 g of HP 55 and 5 g of Citroflex A4 in 1000 g of methylene chloride and 600 g of isopropanol. The results of the release test were that in gastric juice 1% was released after 4 hours and in buffer pH 6.5 100% was released after 10 minutes.

In Examples 10-19 procedures similar to those illustrated above were employed. Ingredients and release data are given in Tables 1 and 2.

BIOPHARMACEUTICAL STUDIES

Two preparations according to the invention, Examples 5 and 3 respectively, were studied and compared with a commercially available, easily soluble tablet preparation of digoxin in a study of sustained release properties and bioavailability in humans. Eight healthy test persons of average age 27 years (22-35 years) participated. The three preparations tested were administered in random order. A dosage unit consisting of two tablets of 0.13 and 0.25 mg digoxin respectively of the commercially available preparation or 86 mg of each of the preparations of the invention filled in capsules, each capsule containing about 200 granules, each dosage unit containing 0.38 mg of digoxin, were administered daily at breakfast for nine consequtive days. From 10 p.m. (22.00) on the ninth day the test persons were fasting. In the morning of the tenth day the last dosage was administered together with 100 ml of water. The fast continued for further three hours. Blood samples were collected just before administration and every hour for the next 12 hours. A last blood sample was taken 24 hours after administration. All the urine produced was collected during said 24 hours. During the following seven days no digoxin was administered. Thereafter administration of the possible next preparation started.

Plasma and urine samples were analyzed with a radioimmunological method with a $^{125}I$ labelled kit (Pharmacia).

The urine samples were treated before analysis according to the method described by Nyberg (Acta Pharm Succ. 14, 119 (1977). The method of analysis employed does not differentiate between digoxin and its decomposition products, however, all results are expressed as concentrations of digoxin.

RESULTS AND DISCUSSION

FIG. 1 shows a diagram with curves of mean plasma concentration of digoxin after administration at steady state of one dosage, said dosage being the tablet ○, the preparation of Example 5 □ and the preparation of Example 3 Δ. The diagram shows that the preparations of the present invention give a more even plasma concentration than does the commercially available tablet. The peak of concentration measured one hour after administration of the tablet is reduced and delayed with the preparations of the invention.

Thus the preparations of the invention provide a substantial reduction in maximum concentration of digoxin as compared with the tablet.

As a measure of bioavailability the mean of the area under the plasma concentration curve for each preparation was calculated. Further the amount of digoxin excreted in urine during the time of administration was measured. (One test person was excluded for incomplete urine collection).

|  | Area under plasma concentration curve | Amount of digoxin excreted in urine | |
|---|---|---|---|
|  | $\mu mol.l^{-1}h$ | $\mu g$ | % of dosage |
| Tablet | 31.3 | 241 | 63.4 |
| Example 5 | 32.4 | 235 | 60.3 |
| Example 3 | 32.1 | 228 | 61.6 |

These results show that the preparations of the invention and the tablet had about equal bioavailability.

The study thus shows that the present invention provides a possibility of lowering the concentration peak of absorbtion without impairing the bioavailability of the active component.

INDUSTRIAL APPLICABILITY

The invention is useful in the pharmaceutical industry and in health care.

TABLE 1

| Example | Core material | | First layer | Second layer |
|---|---|---|---|---|
| 10 | Celluloseavicel | 15.6% |  Polyethyleneglycol | PVAP + cetanol |
|  | Corn starch | 12.5% | 475 g  + digoxin | 72 g + 5 g |
|  | Lactose | 71.9% | 25 g + 2.5 g |  |
| 11 | as in Ex. 10 |  | 475 g as in Ex. 10 | HP-55 + cetanol |
|  |  |  |  | 72 g + 5 g |
| 12 | as in Ex. 10 |  | 475 g as in Ex. 10 | CAP + cetanol |
|  |  |  |  | 72 g + 5 g |
| 13 | as in Ex. 10 |  | 475 g as in Ex. 10 | Eudragit L 100 |
|  |  |  |  | + cetanol 72 g + 5 g |
| 14 | Sugar K 4 |  | 475 g as in Ex. 10 | HP 55 + cetanol |
|  |  |  |  | 72 g + 5 g |
| 15 | Xylitol 0.75-1.2 mm |  | 475 g as in Ex. 10 | HP 55 + cetanol |
|  |  |  |  | 72 g + 5 g |
| 16 | Paraffinwax pellets |  | 475 g as in Ex. 10 | HP 55 + cetanol |
|  |  |  |  | 72 g + 5 g |
| 17 | Sugar (non pareil) |  | 500 g Polyethyleneglycol | HP-55 + Eudragit S 100 |
|  |  |  | + digoxin | 10 g + 10 g |
|  |  |  | 5 g + 1.5 g |  |
| 18 | Sugar (non pareil) |  | 500 g as in Ex. 17 | PVAP + Eudragit S 100 |
|  |  |  |  | 14 g + 6 g |
| 19 | Sugar (non pareil) |  | 500 g as in Ex. 17 | MPM 05 + Eudragit S 100 |

TABLE 1-continued

| Example | Core material | First layer | Second layer |
|---------|---------------|-------------|--------------|
|         |               |             | 24 g + 16 g  |

TABLE 2

| | % Active ingredient released in 500 ml of the release medium Beaker with propeller 100 rpm, 37° C. ± 0.1°C. | | | | | | | |
|---|---|---|---|---|---|---|---|---|
| | Artificial gastric juice pH 1.0 | | | | Phosphate buffer pH 6.5 | | | |
| Example | ½h | 1 h | 2 h | 4 h | 10 min | 30 min | 60 min | 120 min |
| 10 | <1 | 1 | 2 | 3 | 97 | 101 | | |
| 11 | <1 | 1 | 1 | 1 | 100 | 101 | | |
| 12 | 2 | 2 | 2 | 3 | 96 | 101 | | |
| 13 | 1 | 1 | 1 | 2 | 87 | 100 | | |
| 14 | 5 | 6 | 9 | 16 | 94 | 97 | | |
| 15 | <1 | <1 | 1 | 4 | 93 | 100 | | |
| 16 | <1 | <1 | <1 | 65 | 105 | | | |
| 17 | | | | 7 | 13* | 48* | 70* | 93* |
| 18 | | | | 3 | 18* | 45* | 72* | 97* |
| 19 | | | | 6 | 18* | 35* | 55* | 94* |

*After 2 hours in gastric juice

We claim:

1. A pharmaceutical preparation comprising a cardiac glycoside with a polymer coating, characterized in that said pharmaceutical preparation is in the form of a plurality of small bodies, each body comprising a fraction of a therapeutically effective dosage of the cardiac glycoside, whereby each body has a core made up of pharmaceutically indifferent material, and on said core a first layer made up of a composition comprising the cardiac glycoside, and thereon a second layer comprising an anionic carboxylic polymer being difficultly soluble or insoluble below a given pH value in the interval of pH 4–7.5 but being soluble at a pH above said given value.

2. A solid pharmaceutical preparation according to claim 1, characterized in that each of the first layer and the second layer is a layer applied by spraying a solution of the components thereof.

3. A pharmaceutical preparation in accordance with claim 1 or 2 characterized in that said first layer further comprises a water soluble polymer having the ability to increase the solubility or releasability of the cardiac glycoside.

4. A process for preparing a pharmaceutical preparation comprising a cardiac glycoside with a polymer coating, characterized in that said pharmaceutical preparation is given the form of a plurality of small bodies, each body comprising a fraction of a therapeutically effective dosage of the cardiac glycoside, by providing a large number of cores made up of pharmaceutically indifferent material, with a first layer made up of a composition comprising the cardiac glycoside, whereupon the bodies comprising said core and first layer are provided with a second layer comprising an anionic carboxylic polymer being difficultly soluble or insoluble below a given pH value in the interval of pH 4–7.5 but being soluble at a pH above said given value.

5. A process according to claim 4, characterized in that each of the first and the second layer is applied by adding a solution of the components of the layer.

6. A process according to claim 5, characterized in that each solution is applied by spraying.

7. A process according to claim 5 or 6, characterized in that the first and the second layer are applied in a fluid bed apparatus.

8. A method of treatment of cardiac disorders comprising administrating to a mammal including man a therepeutically effective dose of the preparation of claim 1.

9. A pharmaceutical preparation comprising a cardiac glycoside with a polymer coating, characterized in that said pharmaceutical preparation is in the form of a plurality of small bodies, each body comprising a fraction of a therapuetically effective dosage of the cardiac glycoside, whereby each body has a core made up of pharmaceutically indifferent material in a sieve fraction between 0.1 and 3.0 mm, and on said core a first layer made up of a composition comprising the cardiac glycoside, and thereon a second layer comprising an anionic carboxylic polymer being difficultly soluble or insoluble below a given pH value in the interval of pH 4–7.5 but being soluble at a pH above said given value, the weight of the second layer being $1.10^{-2}$ to $30.10^{-2}$ times the weight of the core plus the first layer.

* * * * *

UNITED STATES PATENT AND TRADEMARK OFFICE
CERTIFICATE OF CORRECTION

PATENT NO. : 4,263,273

DATED : April 21, 1981

INVENTOR(S) : Curt H. Appelgren et al.

It is certified that error appears in the above—identified patent and that said Letters Patent is hereby corrected as shown below:

Column 9, TABLE 2, Example 16, in the 4th Col., delete "65" and insert -- 1--; in the 5th col., delete "105" and insert --65--; and in the 6th col., insert --105--.

Signed and Sealed this

Eighth Day of September 1981

[SEAL]

*Attest:*

GERALD J. MOSSINGHOFF

*Attesting Officer*  *Commissioner of Patents and Trademarks*

UNITED STATES PATENT AND TRADEMARK OFFICE
CERTIFICATE OF CORRECTION

PATENT NO. : 4,263,273

DATED : April 21, 1981

INVENTOR(S) : Curt H. Appelgren et al.

It is certified that error appears in the above—identified patent and that said Letters Patent is hereby corrected as shown below:

On the title page, Item [73], "Aktiebolaget Astra" should read
--- Aktiebolaget Hassle ---.

Column 2, line 25, "contains at about" should read --- contains about ---.

Column 7, line 33, "consequtive" should read --- consecutive ---.

Signed and Sealed this

Twentieth Day of October 1981

[SEAL]

Attest:

Attesting Officer

GERALD J. MOSSINGHOFF

Commissioner of Patents and Trademarks